(12) United States Patent
Kawagishi

(10) Patent No.: US 9,361,580 B2
(45) Date of Patent: Jun. 7, 2016

(54) MEDICAL DIAGNOSIS SUPPORT APPARATUS AND METHOD OF CONTROLLING THE SAME

(71) Applicant: CANON KABUSHIKI KAISHA, Tokyo (JP)

(72) Inventor: Masami Kawagishi, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 275 days.

(21) Appl. No.: 13/749,942

(22) Filed: Jan. 25, 2013

(65) Prior Publication Data

US 2013/0212056 A1   Aug. 15, 2013

(30) Foreign Application Priority Data

Feb. 14, 2012 (JP) ................................. 2012-029836

(51) Int. Cl.
*G06N 5/02* (2006.01)
*G06F 19/00* (2011.01)

(52) U.S. Cl.
CPC ............... *G06N 5/02* (2013.01); *G06F 19/345* (2013.01); *G06F 19/321* (2013.01)

(58) Field of Classification Search
CPC .......... G05N 5/02; G05N 5/04; G06F 19/321; G06F 19/345; G06Q 50/22; G06Q 50/24
USPC .......................................... 705/2; 706/46, 52
See application file for complete search history.

(56) References Cited

U.S. PATENT DOCUMENTS

| | | | | |
|---|---|---|---|---|
| 5,235,510 | A * | 8/1993 | Yamada et al. | 600/300 |
| 6,601,055 | B1 * | 7/2003 | Roberts | 706/45 |
| 6,965,857 | B1 * | 11/2005 | Decary | 704/9 |
| 2004/0193022 | A1 | 9/2004 | Torii et al. | 600/300 |
| 2004/0260666 | A1 * | 12/2004 | Pestotnik et al. | 706/46 |
| 2005/0010445 | A1 * | 1/2005 | Krishnan et al. | 705/2 |
| 2006/0143046 | A1 * | 6/2006 | Kawakami et al. | 705/2 |
| 2007/0053567 | A1 * | 3/2007 | Adachi et al. | 382/128 |
| 2007/0083396 | A1 * | 4/2007 | Kanada et al. | 705/3 |

(Continued)

FOREIGN PATENT DOCUMENTS

| | | |
|---|---|---|
| JP | 3332104 | 10/2002 |
| JP | 2004-288047 | 10/2004 |

(Continued)

OTHER PUBLICATIONS

Szolovits P., "Uncertainty and Decisions in Medical Informatics", Methodsof Information in Medicine, 34:111-21, 1995.*

(Continued)

*Primary Examiner* — Stanley K Hill
*Assistant Examiner* — Dave Misir
(74) *Attorney, Agent, or Firm* — Fitzpatrick, Cella, Harper & Scinto

(57) ABSTRACT

A medical diagnosis support apparatus is provided. In the medical diagnosis support apparatus, an acquisition unit acquires medical information associated with a diagnosis target as input information. An inference unit infers a diagnosis name of the diagnosis target based on the acquired input information. A calculation unit calculates the influence rate of each input information with respect to each inference. A creation unit creates a report sentence based on the calculated influence rate.

3 Claims, 8 Drawing Sheets

(56) References Cited

U.S. PATENT DOCUMENTS

| | | | |
|---|---|---|---|
| 2008/0031503 A1* | 2/2008 | Kanada et al. | 382/128 |
| 2008/0249807 A1* | 10/2008 | Niwa et al. | 705/3 |
| 2008/0253631 A1 | 10/2008 | Oosawa | 382/128 |
| 2010/0189366 A1* | 7/2010 | Iizuka et al. | 382/209 |
| 2010/0256459 A1* | 10/2010 | Miyasa et al. | 600/300 |
| 2010/0256991 A1* | 10/2010 | Ishikawa et al. | 705/3 |
| 2010/0332143 A1* | 12/2010 | Onell et al. | 702/19 |
| 2010/0332441 A1* | 12/2010 | Kawagishi et al. | 706/52 |
| 2011/0161278 A1* | 6/2011 | Kawagishi | 706/52 |
| 2011/0199390 A1* | 8/2011 | Iizuka et al. | 345/629 |
| 2011/0213748 A1* | 9/2011 | Kawagishi et al. | 706/52 |
| 2012/0054652 A1* | 3/2012 | Kawagishi et al. | 715/764 |
| 2012/0134555 A1* | 5/2012 | Iizuka et al. | 382/128 |
| 2012/0136882 A1* | 5/2012 | Kawagishi et al. | 707/758 |
| 2012/0254101 A1 | 10/2012 | Kawagishi | |

FOREIGN PATENT DOCUMENTS

| | | |
|---|---|---|
| JP | 2008-259622 | 10/2008 |
| JP | 2009-271621 | 11/2009 |
| JP | 2010-200840 | 9/2010 |

OTHER PUBLICATIONS

Kong G. et al., "Clinical Decision Support Systems: A Review on Knowledge Representation and Inference Under Uncertainties", International Journal of Computational Intelligence Systems, vol. 1, No. 2 (May 2008), 159-167.*

Mangiameli P. et al., "Model selection for medical diagnosis decision support systems", Decision Support Systems, 36, 2004, 247-259.*

Office Action issued Nov. 16, 2015 in counterpart Japanese patent application 2012-029836, with partial translation.

* cited by examiner

AN ABNORMAL SHADOW IS FOUND IN "REGION".

("ITEM NAME" IS "STATE NAME")+

FOR THE ABOVE REASONS, "INFERENCE RESULT" IS SUSPECTED.

| "STATE NAME" | MIDDLE | LAST |
|---|---|---|
| SPHERE | SPHERICAL | IS SPHERICAL. |
| LOBULATION | LOBULATED | IS LOBULATED. |
| IRREGULAR SHAPE | IRREGULAR | IS IRREGULAR. |
| STRONG | STRONG | IS STRONG. |
| INTERMEDIATE | INTERMEDIATE | IS INTERMEDIATE. |
| WEAK | WEAK | IS WEAK. |
| PRESENCE | PRESENT | IS PRESENT. |
| SUSPICION | SUSPICIOUS | IS SUSPICIOUS. |
| ABSENCE | NONE | IS ABSENT. |
| NORMAL VALUE | NORMAL IN TERMS OF ("MEASURED VALUE") | IS NORMAL ("MEASURED VALUE"). |
| ABNORMAL VALUE | ABNORMAL IN TERMS OF ("MEASURED VALUE") | IS ABNORMAL ("MEASURED VALUE"). |

F I G. 4

F I G. 6

AN ABNORMAL SHADOW IS FOUND IN "REGION".
N ("ITEM NAME" IS "STATE NAME")*
P ("ITEM NAME" IS "STATE NAME")*
FOR THE ABOVE REASONS, "INFERENCE RESULT" IS SUSPECTED.

| "STATE NAME" | MIDDLE | N LAST | P LAST |
|---|---|---|---|
| SPHERE | SPHERICAL | SPHERICAL | IS SPHERICAL. |
| LOBULATION | LOBULATED | LOBULATED | IS LOBULATED. |
| IRREGULAR SHAPE | IRREGULAR | IRREGULAR | IS IRREGULAR. |
| STRONG | STRONG | STRONG | IS STRONG. |
| INTERMEDIATE | INTERMEDIATE | INTERMEDIATE | IS INTERMEDIATE. |
| WEAK | WEAK | WEAK | IS WEAK. |
| PRESENCE | PRESENT | PRESENT | IS PRESENT. |
| SUSPICION | SUSPICIOUS | SUSPICIOUS | IS SUSPICIOUS. |
| ABSENCE | NONE | NONE | IS ABSENT. |
| NORMAL VALUE | NORMAL IN TERMS OF ("MEASURED VALUE") | NORMAL IN TERMS OF ("MEASURED VALUE") | IS NORMAL ("MEASURED VALUE"). |
| ABNORMAL VALUE | ABNORMAL IN TERMS OF ("MEASURED VALUE") | ABNORMAL IN TERMS OF ("MEASURED VALUE") | IS ABNORMAL ("MEASURED VALUE"). |

FIG. 8

| j | $l_j$ (FINDING NAME) | jk | $S_{jk}$ (STATE NAME) |
|---|---|---|---|
| 1 | SHAPE | 11 | SPHERICAL SHAPE |
| | | 12 | LOBULATED |
| | | 13 | IRREGULAR |
| 2 | LOBATION | 21 | STRONG |
| | | 22 | INTERMEDIATE |
| | | 23 | WEAK |
| | | 24 | NONE |
| 3 | SMOOTHNESS | 31 | STRONG |
| | | 32 | INTERMEDIATE |
| | | 33 | WEAK |
| | | 34 | NONE |
| ... | | | |
| m | ENGULFMENT (BLOOD VESSEL) | m1 | PRESENT |
| | | m2 | SUSPICIOUS |
| | | m3 | NONE |
| ... | | | |
| n | KL-6 | n1 | NORMAL VALUE |
| | | n2 | ABNORMAL VALUE |

FIG. 9

| j | k | $I_j$ (FINDING NAME) | $S_{jk}$ (STATE NAME) | $I(D_1|S_{jk})$ | $I(D_2|S_{jk})$ | $I(D_3|S_{jk})$ |
|---|---|---|---|---|---|---|
| 1 | 1 | SHAPE | SPHERICAL SHAPE | −0.25 | 0.20 | 0.05 |
| 2 | 2 | LOBATION | INTERMEDIATE | 0.13 | −0.15 | 0.02 |
| 3 | 1 | SMOOTHNESS | STRONG | −0.19 | 0.31 | −0.12 |
| m | 3 | ENGULFMENT (BLOOD VESSEL) | NONE | −0.08 | 0.13 | −0.05 |
| m | 2 | KL-6 | ABNORMAL VALUE | −0.12 | −0.08 | 0.20 |

$P(D_1|E_f) = 0.25$
$P(D_2|E_f) = 0.45$
$P(D_3|E_f) = 0.30$

MEDICAL DIAGNOSIS SUPPORT APPARATUS AND METHOD OF CONTROLLING THE SAME

BACKGROUND OF THE INVENTION

1. Field of the Invention

The present invention relates to a medical diagnosis support apparatus which provides information for supporting diagnosis and a method of controlling the same.

2. Description of the Related Art

In the medical field, doctors perform the image diagnosis of performing diagnosing by interpreting the medical images obtained by imaging apparatuses such as an X-ray CT apparatus and an MRI. When performing image diagnosis, a doctor specifies the symptom of a lesion depicted in an image by comprehensively determining the findings (to be referred to as "interpretation findings" hereinafter) obtained from the image and various kinds of measurement values in accordance with an interpretation request from a primary doctor. The doctor then compiles the process of reaching the diagnosis into an interpretation report to the primary doctor as the request source by using interpretation findings and measurement values.

Such a diagnosis support apparatus designed to support image diagnosis has been developed. For example, Japanese Patent Laid-Open No. 2010-200840 discloses a technique of presenting negative information and positive information concerning the estimation result obtained by an apparatus based on information which has been input (to be referred to as "input information" hereinafter). This makes it possible to present the inference result and also present information influencing the derivation of the inference result from the apparatus based on the input information.

The doctor creates an interpretation report in consideration of the inference result presented by the diagnosis support apparatus. This raises the problem that a heavy burden is imposed on the doctor when creating report sentences. For this reason, attempts have been made to automatically create report sentences by using an inference result from a diagnosis support apparatus. For example, Japanese Patent No. 3332104 discloses a technique of creating interpretation report sentences including an inference result by combining the inference result with a template.

However, the interpretation report sentences automatically created by the method disclosed in Japanese Patent No. 3332104 do not write how the inference result has been derived. For this reason, the primary doctor cannot know the process of reaching the conclusion even by reading this report. That is, the report sentences are difficult for the primary doctor as the request source to understand. The doctor therefore needs to perform the editing operation of, for example, adding sentences for explaining the ground of diagnosis to automatically created report sentences.

SUMMARY OF THE INVENTION

The present invention supports a doctor to efficiently create interpretation report sentences which are easy for a primary doctor as a request source to understand.

According to an aspect of the present invention, there is provided a medical diagnosis support apparatus which provides information for supporting medical diagnosis, the apparatus comprising: an acquisition unit configured to acquire medical information associated with a diagnosis target as input information; an inference unit configured to infer a diagnosis name of the diagnosis target based on the acquired input information; a calculation unit configured to calculate an influence rate of the acquired input information with respect to each inference; and a creation unit configured to create a report sentence based on the calculated influence rate.

Further features of the present invention will become apparent from the following description of exemplary embodiments (with reference to the attached drawings).

BRIEF DESCRIPTION OF THE DRAWINGS

FIG. 4 is a view showing an example of a template according to the first embodiment;

FIG. 6 is a view showing an example of a template according to the second embodiment;

FIG. 8 is a view showing an example of the relationship between interpretation finding names and state names in the first embodiment; and FIG. 9 is a view showing an example of input information, inference results, and influence rates in the first embodiment.

DESCRIPTION OF THE EMBODIMENTS

Various exemplary embodiments, features, and aspects of the invention will be described in detail below with reference to the drawings.

The embodiments of the present invention will be described below with reference to the accompanying drawings. However, the scope of the present invention is not limited to any specific embodiments.

First Embodiment

A medical diagnosis support apparatus according to the first embodiment acquires, as input information, medical information concerning a case as a diagnosis target, and performs diagnosis support concerning the case.

The following is an example in which the medical diagnosis support apparatus acquires a plurality of interpretation findings and a tumor marker value which are associated with an abnormal shadow of the lung as input information, performs inference associated with the abnormality type (diagnosis name) of the abnormal shadow, and presents diagnosis support information based on the inference result. Obviously, an inference target is not limited to this, and the following diagnosis names, interpretation findings, tumor marker values, and the like each are merely an example for explaining the steps in the processing performed by the medical diagnosis support apparatus.

Figure 1:
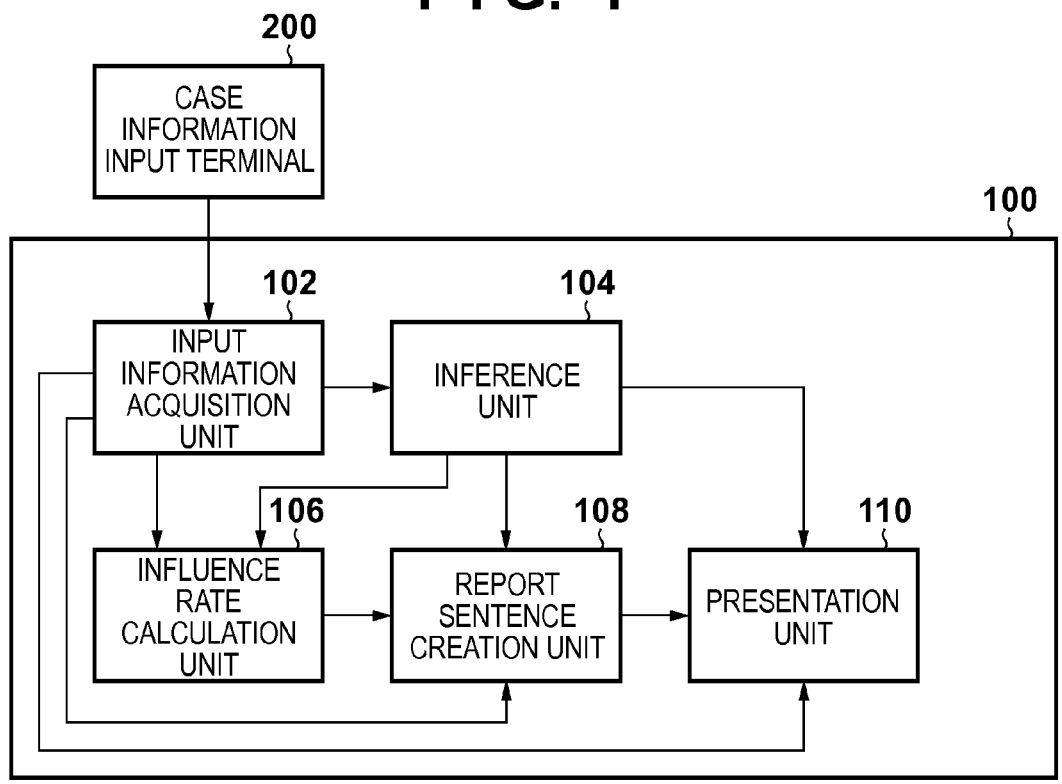
FIG. 1 is a block diagram showing the arrangement of a medical diagnosis support apparatus according to the first embodiment.

FIG. 1 shows the arrangement of the medical diagnosis support apparatus according to the first embodiment. A medical diagnosis support apparatus 100 in this embodiment is connected to a case information input terminal 200.

The case information input terminal 200 acquires medical information (medical images, electronic chart information, and the like) associated with the abnormal shadow of the lung concerning a case as a diagnosis target from a server (not shown). Alternatively, external storage devices such as an FDD, HDD, CD drive, DVD drive, MO drive, and ZIP drive may be connected to the apparatus to allow it to acquire data from them. The apparatus then displays these pieces of information on a monitor in a form that allows the user (doctor) to perform radiogram interpretation, and acquires the clinical data such as interpretation findings and tumor marker values input by the user. In this embodiment, the user inputs the interpretation findings of the medical image displayed on the monitor by using a mouse and a keyboard. Note that this processing is implemented by making the case information input terminal 200 have functions which can be selected by a GUI using, for example, an interpretation finding input support method based on a template form. In response to a request from the user, the case information input terminal 200 transmits input information associated with the abnormal shadow of the lung and accompanying data (e.g., typical images) to the medical diagnosis support apparatus 100 via a LAN or the like. Although the user inputs interpretation findings in this embodiment, it is possible to use the interpretation findings automatically calculated by performing image processing for medical images and using the results. In addition, such image processing results may be directly used as input information.

The medical diagnosis support apparatus 100 includes an input information acquisition unit 102, an inference unit 104, an influence rate calculation unit 106, a report sentence creation unit 108, and a presentation unit 110.

The input information acquisition unit 102 acquires the input information associated with the abnormal shadow of the lung and the accompanying data which are input from the case information input terminal 200 to the medical diagnosis support apparatus 100, and outputs the data to the inference unit 104, the influence rate calculation unit 106, and the presentation unit 110.

The inference unit 104 executes inference concerning the abnormal shadow of the lung as the diagnosis target based on the input information acquired by the input information acquisition unit 102, and calculates a probability (inference result) as the diagnosis name of the abnormal shadow. The calculated inference result is output to the influence rate calculation unit 106, the report sentence creation unit 108, and the presentation unit 110.

The influence rate calculation unit 106 calculates the influence rate of each input information with respect to the inference by using the input information acquired by the input information acquisition unit 102 and the inference result acquired by the inference unit 104. The acquired influence rate is output to the report sentence creation unit 108.

The report sentence creation unit 108 selects information which influences an inference by using the influence rate of each input information acquired by the influence rate calculation unit 106 with respect to the inference. In addition, the report sentence creation unit 108 creates interpretation report sentences based on the inference result acquired by the inference unit 104 and the selected information. The selected information and the created interpretation report sentences are output to the presentation unit 110.

The presentation unit 110 generates and displays information to be presented. More specifically, the presentation unit 110 generates information to be presented based on the input information and the accompanying data acquired by the input information acquisition unit 102, the inference result acquired by the inference unit 104, the information influencing the inference which is selected by the report sentence creation unit 108, and the created interpretation report sentences.

Note that at least some of the units of the medical diagnosis support apparatus 100 shown in FIG. 1 may be implemented as independent devices. Alternatively, each unit may be implemented as software which implements each function. Assume that in this embodiment, each unit is implemented by software.

Figure 2:
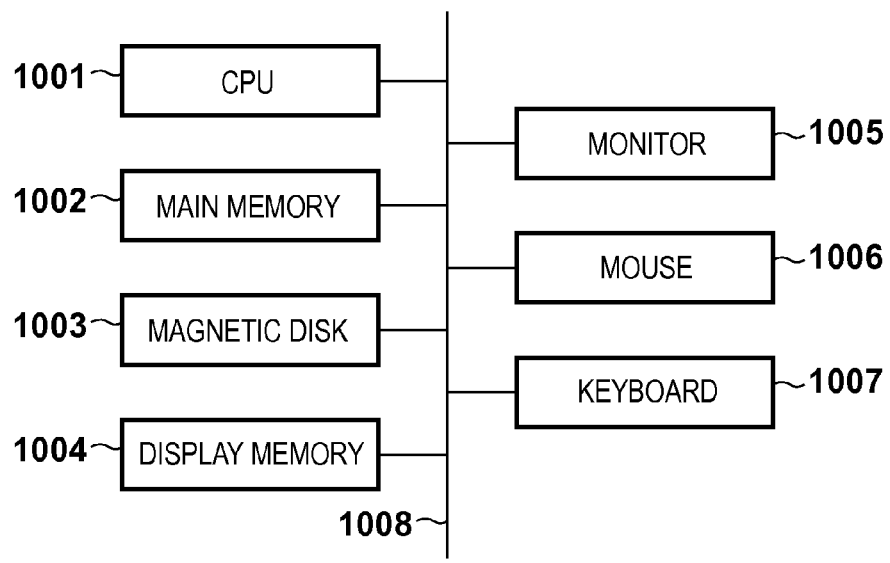
FIG. 2 is a block diagram showing the basic arrangement of a computer which implements each processing unit of the diagnosis support apparatus by using software.

FIG. 2 shows the basic arrangement of a computer for implementing the function of each unit shown in FIG. 1 by executing software. A CPU 1001 mainly controls the operation of each constituent element. A main memory 1002 stores control programs to be executed by the CPU 1001, and provides a work area at the time of execution of a program by the CPU 1001. A magnetic disk 1003 stores an OS (Operating System), device drives for peripheral devices, various kinds of application software including programs for processing to be described later, and the like. A display memory 1004 temporarily stores display data. A monitor 1005 is, for example, a CRT monitor or liquid crystal monitor, and displays an image, text, and the like based on data from the display memory 1004. A mouse 1006 and a keyboard 1007 are used by the user to perform pointing input and input characters and the like. The above constituent elements are communicatively connected to each other via a common bus 1008.

Figure 3:
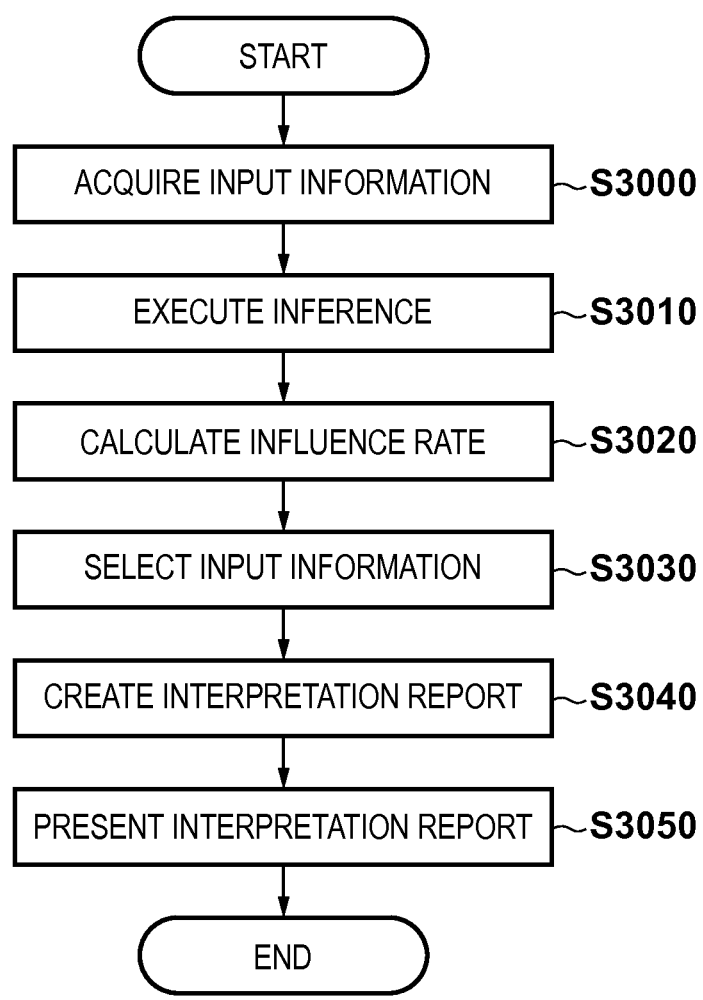
FIG. 3 is a flowchart showing an overall processing procedure according to the first embodiment.

The overall processing performed by the medical diagnosis support apparatus 100 will be described next with reference to the flowchart of FIG. 3. In this embodiment, the CPU 1001 implements this processing by executing a program for implementing the function of each unit which is stored in the main memory 1002.

In the following description, interpretation finding/tumor marker names are represented by $I_j$ (j=1 to n), and n types of interpretation finding/tumor marker names $I_1$ to $I_n$ are handled. In addition, k states which $I_j$ can take are written as $S_{jk}$. The range of k varies in value depending on $I_j$. Assume that in this embodiment, it is possible to input or acquire interpretation finding/tumor marker values like those shown in FIG. 8, and the respective interpretation finding/tumor marker values can take states like those shown in FIG. 8. For example, "shape" of $I_1$ represents the shape of an abnormal shadow, and takes three states, namely $S_{11}$ "sphere", $S_{12}$ "lobulation", and $S_{13}$ "irregular shape". "Lobation" of $I_2$ represents the degree of lobation in an abnormal shadow. In addition, "engulfment (blood Vessel)" of $I_m$ represents the presence/absence of the engulfment of a blood vessel in an abnormal shadow. Furthermore, "KL-6" of $I_n$ represents whether sialylated carbohydrate antigen KL-6 in a serum, which is used as a tumor marker for interstitial pneumonia, falls within reference values (equal to or less than 500 U/ml).

In the following description, a set of $S_{jk}$ is written as E, and input information is represented by $E_f$. Assume however that a plurality of states $S_{jk}$ corresponding to one $I_1$ do not simultaneously exist in one E. For example, if $I_1$ takes $S_{11}$, $S_{22}$, and $S_{23}$, and $I_2$ takes $S_{21}$, $S_{22}$, $S_{23}$, and $S_{24}$, $E\{S_{11}, S_{22}\}$ holds, but $E=\{S_{11}, S_{12}\}$ does not hold. This is because one interpretation finding/tumor marker value takes only one state. In the following description, a diagnosis name will be written as a symbol D. According to this embodiment, the diagnosis name may have other three values respectively representing primary lung cancer, lung cancer metastasis, and others, which are respectively written as $D_1$, $D_2$, and $D_3$. The inference probability of a diagnosis name $D_r$ (r=1, 2, 3) with input information $E_f$ being given will be written as $P(D_r|E_f)$. The influence rate of an element $S_{jk}$ of $E_f$ corresponding to the diagnosis name $D_r$ is written as $I(D_r|S_{jk})$.

In step S3000, the input information acquisition unit 102 acquires input information and accompanying data concerning an abnormal shadow of the lung input to the medical diagnosis support apparatus 100. Assume that the acquired interpretation finding/tumor marker values are $I_1$ "shape": $S_{11}$ "sphere", $I_2$ "lobation": $S_{22}$ "intermediate", $I_m$ "engulfment (blood vessel)": $S_{m3}$ "none", . . . , $I_n$ "KL-6": $S_{n2}$ "abnormal value". In this case, the set $E_f$ of $S_{jk}$ is given as $E_f = \{S_{11}, S_{22}, \ldots, S_{m3}, S_{n2}\}$.

In step S3010, the inference unit 104 infers the probability (inference result) of the abnormal shadow being each diagnosis name based on the input information (that is, Ef) acquired in step S3000. The inference unit 104 then selects a diagnosis name exhibiting the highest inference probability as an inferred diagnosis name $D_f$. As an inference technique at this time, it is possible to use any one of various existing inference techniques such as a Bayesian network, neural network, and support vector machine. This embodiment uses the Bayesian network as an inference technique. The Bayesian network is an inference model using conditional probabilities. It is possible to acquire the inference probability of each diagnosis name when input information is input (the probability of the case being each diagnosis name; also called a posterior probability). In this embodiment, the inference unit 104 acquires the probabilities $P(D_r|E_f)$ of the diagnosis names D1, D2, and D3 of abnormal shadows.

In step S3020, the influence rate calculation unit 106 calculates the influence rate of each element of the input information $E_f$ acquired in step S3000 with respect to each diagnosis name. In this embodiment, the influence rate $I(D_r|S_{jk})$ of $S_{jk}$ with respect to the diagnosis name $D_r$ is defined as the difference between a posterior probability $P(D_r)$ of $D_r$ and an inference probability $P(D_r|S_{jk})$ of $D_r$ obtained when only $S_{jk}$ is input, and is calculated by $$I(D_r|S_{jk}) = P(D_r|S_{jk}) - P(D_r) \quad (1)$$

In this case, if $I(D_r|S_{jk})$ is positive, that is, the posterior probability obtained when only $S_{jk}$ is input is higher than the prior probability, $S_{jk}$ has a positive influence rate for $D_r$. If $I(D_r|S_{jk})$ is negative, that is, the posterior probability obtained when only $S_{jk}$ is input is lower than the prior probability, $S_{jk}$ has a negative influence rate for $D_r$. Note that the above method of calculating influence rates is an example of the processing in this embodiment, and the method to be used is not limited to this.

In step S3030, the report sentence creation unit 108 selects information influencing an inference as the ground of the inference by using the influence rate of each piece of input information acquired in step S3020 with respect to the inference.

In this embodiment, the report sentence creation unit 108 selects part of input information as information influencing an inference. More specifically, the report sentence creation unit 108 selects pieces of input information, out of the pieces of input information having positive influence rates for the inferred diagnosis name $D_f$, which have the top three influence rates. Assume that as a result of the processing up to step S3020, input information, inference results, and influence rates like those shown in FIG. 9 have been obtained. At this time, since the inference probabilities of $D_1$, $D_2$, and $D_3$ are 0.25, 0.45, and 0.30, respectively, $D_2$ is the diagnosis name (inferred diagnosis name) exhibiting the highest inference probability. In this case, the pieces of input information having the top three positive influence rates for $D_2$ are $I_3$ "smoothness": $S_{31}$ "strong" (0.31), $I_1$ "shape": $S_{11}$ "sphere" (0.20), and $I_m$ "engulfment (blood vessel)": $S_{m3}$ "none" (0.13). These pieces of input information are selected as information influencing the inference.

In step S3040, based on the inference result acquired in step S3010 and the input information selected in step S3030, the report sentence creation unit 108 creates interpretation report sentences including the inference result and the ground of the inference which explains the inference result.

This embodiment creates an interpretation report by using a template like that shown in FIG. 4. In the template, "region" indicates that it can change depending on the accompanying data acquired in step S3000. Likewise, "item name" and "state name" indicate that they can change depending on the information selected in step S3030. Note that "item name" and "state name" respectively correspond to $I_j$ and $S_{jk}$. In addition, "inference result" in the template indicates that it can change depending on the inference result acquired in step S3010. In the embodiment, "inference result" is a diagnosis name (inferred diagnosis name) exhibiting the highest inference probability. In addition, "("item name" is "state name")+" indicates that the character string ""item name" is "state name"" is repeated one or more times (corresponding to the number of pieces of input information selected in step S3030). When performing this repeating operation, the apparatus changes the order of writing based on the influence rates of the respective pieces of input information. More specifically, the respective pieces of information are written in descending order of the influence rates. That is, information exhibiting the highest influence rate, information exhibiting the second highest influence rate, . . . are written in the order named. In this embodiment, since pieces of input information exhibiting the top three influence rates are selected as information influencing the inference, such character string is repeated three times at maximum. Note that as shown in FIG. 4, different characters fit "state name" depending on "middle" (middle of repetition) and "last" (end of repetition).

Referring to the example shown in FIG. 9, $D_2$ (that is, lung cancer metastasis) fits "inference result". In addition, the apparatus obtains $I_3$ "smoothness": $S_{31}$ "strong" (0.31), $I_1$ "shape": $S_{11}$ "sphere" (0.20), and $I_m$ "engulfment (blood vessel)": $S_{m3}$ "none" (0.13) from the results selected as information influencing the inference. If "left lung field" is filled in "region name" based on the accompanying information, the apparatus creates the following sentences as interpretation report sentences:

"An abnormal shadow is found in the left lung field. The smoothness is strong, the shape is spherical, and there is no engulfment (blood vessel). For the above reasons, lung cancer metastasis is suspected."

Note that the method of creating interpretation report sentences by using the above template is an example of the processing in this embodiment, and the method to be used is not limited to this.

In step S3050, the presentation unit 110 creates and displays information to be presented. More specifically, the presentation unit 110 creates information to be presented based on the input information and accompanying data acquired in step S3000, the inference result acquired in step S3010, the information selected in step S3030 the interpretation report sentences created in step S3040.

Figure 5:
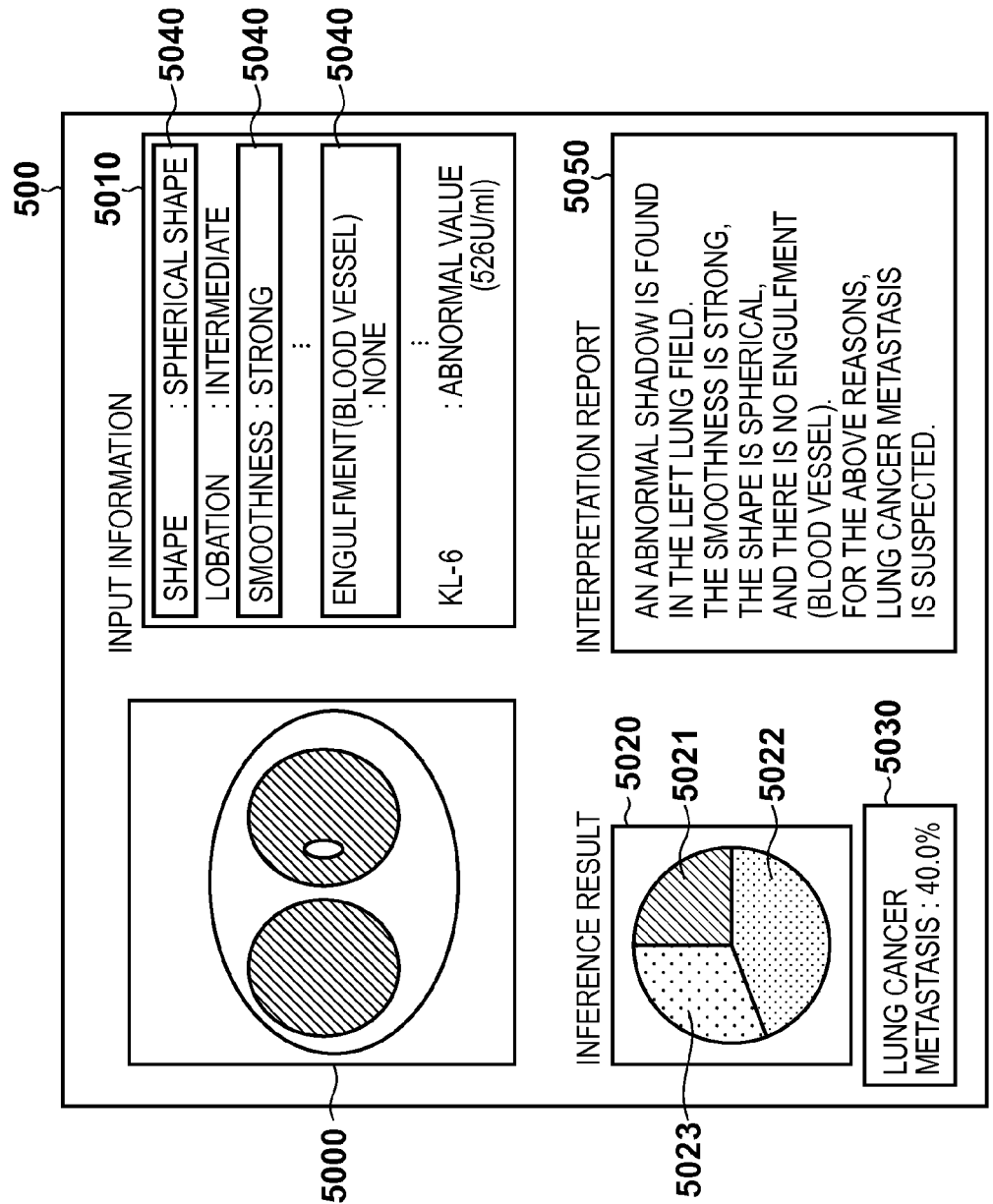
FIG. 5 is a view showing an example of presentation information according to the first embodiment.

FIG. 5 shows an example of presentation information to be displayed on the monitor 1005 in this embodiment. Presentation information 500 includes a representative image 5000 of the abnormal shadow in the lung acquired in step S3000, and input information 5010 of the abnormal shadow in the lung. In addition, presentation information 400 includes an inference result 5020 inferred in step S3010. In the example shown in FIG. 5, the apparatus displays in a pie chart, as the inference result 5020, an inference probability 5021 of a primary lung cancer in the inference result, an inference probability 5022 of a lung cancer metastasis, and an inference probability 5023 of others. In addition, the presentation information 500 includes an inferred diagnosis name ("lung cancer metastasis" in the example shown in FIG. 5) and a probability 5030 of the inferred diagnosis name (the inference probability of the lung cancer metastasis in the example shown in FIG. 5). The presentation information 500 also includes a frame 5040 indicating information (the ground of the inference) influencing the inference selected in step S3030 and interpretation report sentences 5050 created in step S3040.

This embodiment creates interpretation report sentences including not only an inference result but also input information influencing the inference result. This allows the doctor to use generated interpretation report sentences as a template so as to efficiently create interpretation report sentences easy for the primary doctor as the request source to understand.

Second Embodiment

A medical diagnosis support apparatus according to the second embodiment creates an interpretation report with a changed modification structure by using medical information having a positive influence on an inference result and medical information having a negative influence on the inference result.

The arrangement of the medical diagnosis support apparatus according to this embodiment is the same as that shown in FIG. 1 in the first embodiment. In addition, the basic arrangement of a computer which implements a medical diagnosis support apparatus 100 by executing software is the same as that shown in FIG. 2 in the first embodiment. Furthermore, the same flowchart as that shown in FIG. 3 is used to explain the overall processing performed by the medical diagnosis support apparatus 100. However, part of the processing in steps S3030 and S3040 differs from that in the first embodiment. Only portions of the overall processing performed by the medical diagnosis support apparatus 100 according to the second embodiment which differ from those in the first embodiment will be described below with reference to the flowchart of FIG. 3.

Each process in steps S3000 to S3020 is the same as that in the first embodiment.

In step S3030, a report sentence creation unit 108 selects input information having a negative influence on an inferred diagnosis name $D_f$ and input information having a positive influence on it by using the influence rate of each input information acquired in step S3020 with respect to an inference.

This embodiment defines a threshold $\theta_n$ concerning negative influences and a threshold $\theta_p$ concerning positive influences and selects part of input information. More specifically, the report sentence creation unit 108 selects input information having an influence rate equal to or less than $\theta_n$ with respect to an inferred diagnosis name $D_f$ as information influencing an inference (input information having a negative influence). Likewise, the report sentence creation unit 108 also selects input information having an influence rate equal to or more than $\theta_p$ as information influencing the inference (input information having a positive influence). Assume that input information, inference results, and influence rates like those shown in FIG. 9 have been obtained. Assume also that $\theta_n$ is −0.05 and $\theta_p$ is 0.20. In this case, pieces of input information whose influence rates with respect to $D_2$ as an inferred diagnosis name are equal to or less than $\theta_n$ are $I_2$ "lobation": $S_{22}$ "intermediate" (−0.15) and $I_n$ "KL-6": $S_{n2}$ "abnormal value" (−0.08). Likewise, pieces of input information whose influence rates with respect to $D_2$ are equal to or more than $\theta_p$ are $I_3$ "smoothness": $S_{31}$ "strong" (0.31) and $I_1$ "shape": $S_{11}$ "sphere" (0.20). The report sentence creation unit 108 selects these pieces of input information as information influencing the inference.

In step S3040, the report sentence creation unit 108 creates interpretation report sentences for explaining the ground of the inference, including the inference result and negative information, based on the inference result acquired in step S3010 and the input information selected in step S3030.

This embodiment creates an interpretation report by using a template like that shown in FIG. 6. "Region", "item name", "state name", and "inference result" in the template are the same as those in FIG. 4. "N ("item name" is "state name")*" indicates that the character string ""item name" is "state name"" is repeated zero or more times (corresponding to the number of pieces of negative input information selected in step S3030) based on input information having a negative influence. This character string is repeated zero times if there is no input information satisfying the condition. When performing this repeating operation, the apparatus changes the order of writing based on the influence rates of the respective pieces of input information. More specifically, the respective pieces of information are written in descending order of the absolute values of the influence rates. That is, information exhibiting the highest absolute value of an influence rate, information exhibiting the second highest absolute value of an influence rate, . . . are written in the order named. Likewise, "P ("item name" is "state name")*" indicates that the character string ""item name" is "state name"" is repeated zero or more times (corresponding to the number of pieces of positive input information selected in step S3030) based on input information having a positive influence. The same method of executing repeating operation is used. Note that as shown in FIG. 6, different characters fit in "state name" depending on "middle" (middle of repetition), "N last" (end of repetition based on input information having a negative influence), and "P last" (end of repetition based on input information having a positive influence). That is, the modification structure for input information is changed in accordance with the signs of influence rates.

As in the first embodiment, if "left lung field" is filled in "region name" based on the accompanying information, the apparatus creates the following sentences as interpretation report sentences:

"An abnormal shadow is found in the left lung field. The lobation is intermediate and KL-6 is abnormal (526 U/ml), but the smoothness is strong and the shape is spherical. For the above reasons, lung cancer metastasis is suspected."

Note that the method of creating interpretation report sentences by using the above template is an example of the processing in this embodiment, and the method to be used is not limited to this.

The processing in step S3050 is the same as that in the first embodiment.

Figure 7:
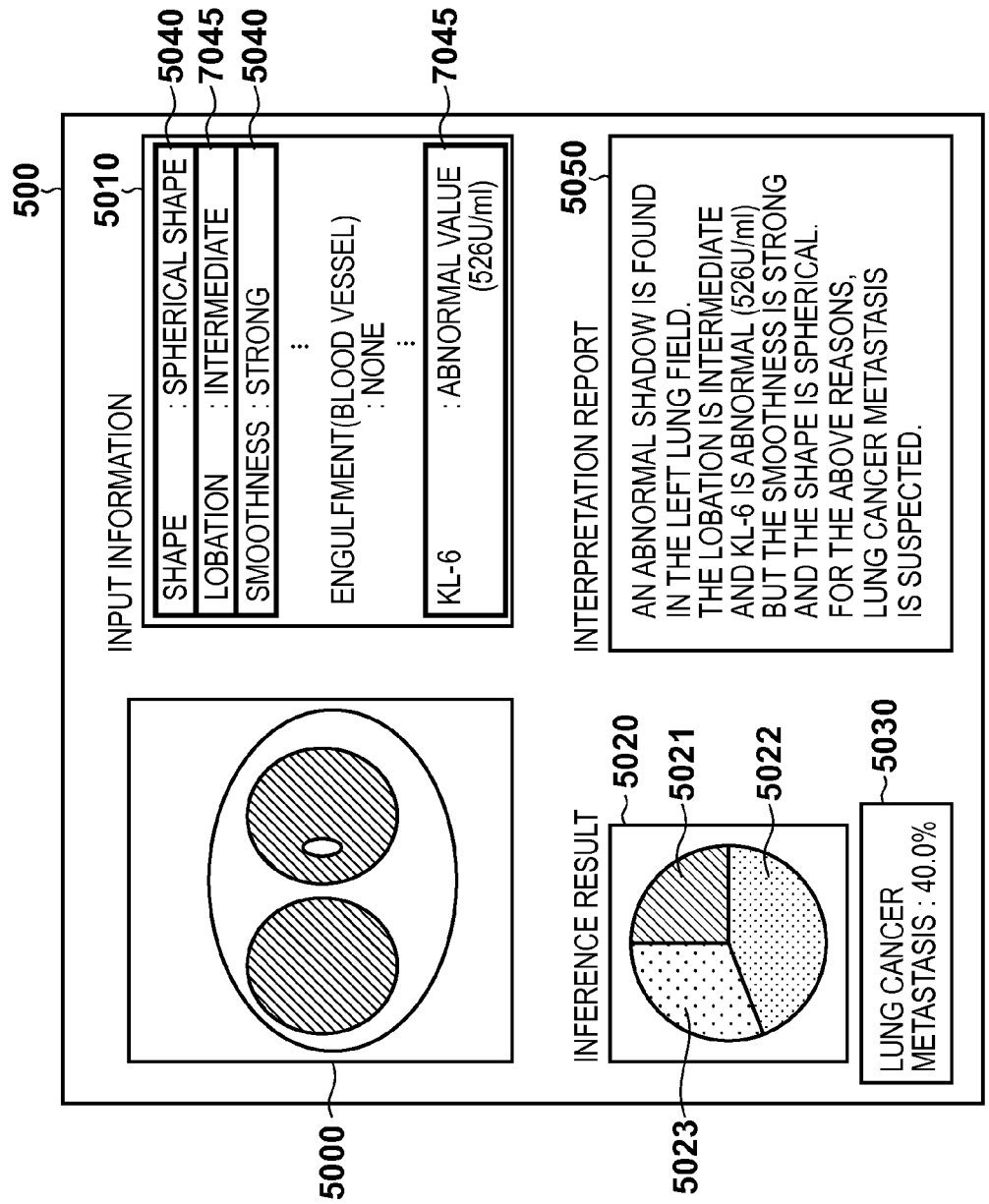
FIG. 7 is a view showing an example of presentation information according to the second embodiment.

FIG. 7 shows an example of presentation information to be displayed on a monitor 1005 in this embodiment. The example shown in FIG. 7 includes a frame 7045 indicating input information having a negative influence on the inference which is selected in step S3030 in addition to the example shown in FIG. 5.

This embodiment creates interpretation report sentences with a changed modification structure by using medical information having a positive influence on an inference result and medical information having a negative influence on the inference result. This allows to discriminate position information concerning an inference result from negative information concerning the inference result. Therefore, the interpretation report sentences are more expected to be understandable for the primary doctor. This allows the doctor to use generated interpretation report sentences as a template so as to efficiently create interpretation report sentences easy for the primary doctor as the request source to understand.

First Modification

According to the above two embodiments, the apparatus calculates influence rate of each element of the input information $E_f$ with respect to each diagnosis name in step S3020. However, the apparatus may create combinations $E_{fs}$ (s=1, 2, . . . ) of the respective elements of $E_f$ and calculate the influence rates of $E_{fs}$. In this case, the number of combinations may be an arbitrary number. Assume that $E_f=\{S_{11}, S_{22}, S_{m3}, S_{n2}\}$, and the number of combinations is 2. In this case, the apparatus creates six $E_{fs}$, namely $E_{f1}=\{S_{11}, S_{22}\}$, $E_{f2}=\{S_{11}, S_{m3}\}$, $E_{f3}=\{S_{11}, S_{n2}\}$, $E_{f4}=\{S_{22}, S_{m3}\}$, $E_{f5}=\{S_{22}, S_{n2}\}$, and $E_{f6}=\{S_{m3}, S_{n2}\}$. The apparatus calculates the influence rates of the respective combinations $E_{fs}$.

Second Modification

According to the above two embodiments, pieces of information are made to fit the template in descending order of influence rates in step S3030. That is, the order of writing complies with the influence rates. However, pieces of information may be made to fit the template by using other methods. For example, priority levels may be set for the respective pieces of input information, and the respective pieces of information may be made to fit the template in descending order of priority levels. That is, the order of writing may comply with the priority levels. Alternatively, the modification structure may be changed in accordance with the magnitudes of influence rates. For example, an emphatic expression such as "in addition" or "furthermore" may be added in front of the item name of information having the highest influence rate. In this case, pieces of information can be written in ascending order of influence rates. For example, the apparatus creates the following report sentences:

"An abnormal shadow is found in the left lung field. There is no engulfment (blood vessel) and the shape is spherical. In addition, the smoothness is strong. For the above reasons, lung cancer metastasis is suspected."

Although the above two embodiments use the templates, they may use other methods. For example, the apparatus may create natural sentences by regarding input information as morphemes and using a morpheme analysis technique and a parsing technique.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-029836, filed Feb. 14, 2012, which is hereby incorporated by reference herein in its entirety.

What is claimed is:

1. A medical diagnosis support apparatus which provides information for supporting medical diagnosis, the apparatus comprising:

at least one CPU and a memory operatively coupled to function as:
   an acquisition unit configured to acquire medical information associated with a diagnosis target as input information;
   an inference unit configured to infer a diagnosis name of the diagnosis target as an inference result based on the acquired input information, wherein the diagnosis name exhibits a highest inference probability;
   a calculation unit configured to calculate an influence rate of the acquired input information with respect to each inference; and
   a creation unit configured to create a report sentence based on the calculated influence rate,
   wherein the creation unit is configured to select terms from the input information,
   wherein the creation unit is configured to
   select a first set of terms from the input information, each of the first set of terms having an influence rate equal to or less than a first threshold concerning negative influences, and select a second set of terms from the input information, each of the second set of terms having an influence rate equal to or more than a second threshold concerning positive influences,
   select a first predetermined number of terms, from the first set of terms, to be applied to the report sentence in descending or ascending order of negative influence rate on the inference result, and select a second predetermined number of terms, from the second set of terms, to be applied to the report sentence in descending or ascending order of positive influence rate on the inference result, and
   determine an order of writing of the selected first and second predetermined number of terms based on the descending or ascending order of the negative influence rate and the descending or ascending order of the positive influence rate, and change a modification structure of the selected first and second predetermined number of terms based on whether terms written in the report sentence have a positive influence rate on the inference result or a negative influence rate on the inference result.

2. A method of controlling a medical diagnosis support apparatus which provides information for supporting medical diagnosis, the method comprising the steps of:
   acquiring medical information associated with a diagnosis target as input information;
   inferring a diagnosis name of the diagnosis target as an inference result based on the acquired input information, wherein the diagnosis name exhibits a highest inference probability;
   calculating an influence rate of the acquired input information with respect to each inference; and creating a report sentence based on the calculated influence rate, wherein the creating step includes selecting terms from the input information, and wherein, in the creating step, terms are selected to be applied to the report sentence based on the calculated influence rate and an order of writing of the selected terms is determined based on the descending or ascending order of the negative influence rate and the descending or ascending order of the positive influence rate, and change a modification structure of the selected first and second predetermined number of terms based on whether terms written in the report sentence have a positive influence rate on the inference result or a negative influence rate on the inference result.

3. A non-transitory computer readable storage medium storing a program for controlling a medical diagnosis support apparatus including a computer executing the program, the program comprising code for performing the following steps:

acquiring medical information associated with a diagnosis target as an interference result as input information, wherein the diagnosis name exhibits a highest inference probability;

inferring a diagnosis name of the diagnosis target based on the acquired input information;

calculating an influence rate of the acquired input information with respect to each inference; and creating a report sentence based on the calculated influence rate, wherein the creating step includes selecting terms from the input information, and wherein, in the creating step, terms are selected to be applied to the report sentence based on the calculated influence rate and an order of writing of the selected terms is determined based on the descending or ascending order of the negative influence rate and the descending or ascending order of the positive influence rate, and change a modification structure of the selected first and second predetermined number of terms based on whether terms written in the report sentence have a positive influence rate on the inference result or a negative influence rate on the inference result.

* * * * *